US007725024B2

(12) United States Patent
Baldwin et al.

(10) Patent No.: US 7,725,024 B2
(45) Date of Patent: May 25, 2010

(54) OPTIMIZING USE AND PERFORMANCE OF OPTICAL SYSTEMS IMPLEMENTED WITH TELECENTRIC ON-AXIS DARK FIELD ILLUMINATION

(75) Inventors: Leo Baldwin, Beaverton, OR (US); Joseph J. Emery, Vancouver, WA (US)

(73) Assignee: Electro Scientific Industries, Inc., Portland, OR (US)

( * ) Notice: Subject to any disclaimer, the term of this patent is extended or adjusted under 35 U.S.C. 154(b) by 910 days.

(21) Appl. No.: 11/483,133

(22) Filed: Jul. 7, 2006

(65) Prior Publication Data

US 2007/0009257 A1    Jan. 11, 2007

Related U.S. Application Data

(60) Provisional application No. 60/697,904, filed on Jul. 8, 2005.

(51) Int. Cl.
*G01N 21/01* (2006.01)
(52) U.S. Cl. ..................................... 396/432
(58) Field of Classification Search ................. 396/432, 396/505; 348/87, 126; 356/237.2–237.5
See application file for complete search history.

(56) References Cited

U.S. PATENT DOCUMENTS

| 5,166,985 | A | | 11/1992 | Takagi et al. |
| 5,177,559 | A | | 1/1993 | Batchelder et al. |
| 5,298,989 | A | * | 3/1994 | Tsukahara et al. .......... 348/126 |
| 5,377,001 | A | * | 12/1994 | Malin et al. .............. 356/237.2 |
| 5,396,334 | A | * | 3/1995 | Sugawara .................. 356/394 |
| 5,408,084 | A | | 4/1995 | Brandorff et al. |
| 5,469,294 | A | | 11/1995 | Wilt et al. |
| 5,737,122 | A | | 4/1998 | Wilt et al. |
| 6,201,892 | B1 | | 3/2001 | Ludlow et al. |
| 6,207,946 | B1 | | 3/2001 | Jusoh et al. |
| 6,222,624 | B1 | * | 4/2001 | Yonezawa ................ 356/237.1 |
| 6,385,507 | B1 | | 5/2002 | Buijtels |
| 6,870,949 | B2 | | 3/2005 | Baldwin |
| 7,342,608 | B2 | * | 3/2008 | Yoshida .................... 348/353 |
| 2002/0080236 | A1 | | 6/2002 | Madsen et al. |

(Continued)

FOREIGN PATENT DOCUMENTS

JP          2002328094          11/2002

OTHER PUBLICATIONS

Search Report and Written Opinion Concerning the Corresponding International Application No. PCT/US2006/026649.

*Primary Examiner*—W. B. Perkey
(74) *Attorney, Agent, or Firm*—Stoel Rives LLP

(57) ABSTRACT

Systems and methods are provided for imaging a planar specular object such as a semiconductor wafer. In one embodiment, an imaging system for imaging a defect on a planar specular object includes a telecentric lens having a sufficiently aspherical surface such that the telecentric lens is substantially corrected for an optical aberration. The imaging system also includes a telecentric stop including an aperture therein to block light reflected from the planar specular object while allowing light reflected from the defect to pass through the aperture. The imaging system further includes a lens group having a system stop positioned between the telecentric stop and the lens group. The lens group is substantially corrected for the optical aberration independent of the telecentric lens.

10 Claims, 6 Drawing Sheets

U.S. PATENT DOCUMENTS

2002/0113970 A1 8/2002 Baldwin et al.
2002/0135757 A1 9/2002 Shires
2004/0160599 A1 8/2004 Hamamatsu et al.

* cited by examiner

OPTIMIZING USE AND PERFORMANCE OF OPTICAL SYSTEMS IMPLEMENTED WITH TELECENTRIC ON-AXIS DARK FIELD ILLUMINATION

RELATED APPLICATION

This application claims the benefit under 35 U.S.C. §119(e) of U.S. Provisional Application No. 60/697,904, filed Jul. 8, 2005, which is hereby incorporated by reference herein in its entirety.

TECHNICAL FIELD

This disclosure relates to imaging optics and associated illumination systems. In particular, this disclosure relates to systems and methods for improving telecentric on-axis dark field illumination.

BACKGROUND INFORMATION

There is a class of semiconductor products that are predominantly planar and specular (flat and shiny). It is frequently necessary or desirable to image these devices in such way that even minor deviations from planar and specular are imaged with adequate contrast. One such class of products are semiconductor wafers that may be provided with indicia that indicate, among other things, wafer number and manufacturer. These indicia are defects in the surface of the wafer and are typically a matrix of laser etched pits. These indicia are known in the art as "soft marks." These marks are imaged to read the codes at various steps along the manufacturing process.

After the semiconductor wafers have been singulated (generally cut by saw and/or laser into individual rectangular devices), it may be necessary or desirable to inspect the edges for small chips and cracks that may propagate over time and cause premature device failure. These inspection processes are automated and use electronic imaging cameras in combination with digital electronic computers that are programmed to perform the necessary inspections, measurements and identifications.

Dark field lighting, in general, is a technique well known to those skilled in the art and is particularly useful to inspect defects on specular objects. The definition of dark field lighting is dependent upon the properties of the illumination source, its position relative to both the object and the observer, or camera, and on the properties of the object being illuminated. In order to meet the definition of dark field lighting, it is necessary that the majority of the illumination incident on the object is reflected in a direction or directions that do not enter the optical aperture of the observer or camera. Dark field illumination can be compared against bright field illumination where the majority of light is reflected directly into the camera.

Dark field lighting can be achieved by placing a light source such that it is pointing at the object at an angle to the line between the camera and the object. This angle is selected to be greater than the angle over which the object will diffuse light. If the object has a generally diffuse reflective nature, then the angle is selected to be larger than the half-angle over which the object will distribute incident illumination by diffuse reflection. If the object is specular (e.g., if the object diffuses incident illumination over a small angle, or with very low efficiency, or both), then the angle may be selected to be very small.

It may be desirable to make the illumination source symmetric. In this case, the source may be manufactured in an annular shape and placed coaxial to the optical axis, or a plurality of sources may be arranged in an annular shape. The diameter of this annulus and its proximity to the object determine the range of angles over which the illumination is incident upon the object. Such lights are known to those skilled in the art as ring lights and are variously configured to be "high angle" or "low angle."

In imaging certain objects, it is desirable to highlight very minor features in a surface which is otherwise substantially planar and specular. These include soft marks and the edges of singulated devices. To achieve this, it is necessary to bring the illumination source as nearly on-axis with the imaging system as possible without causing the illumination source to be directly reflected into the imaging system (e.g., selecting a narrow angle). An effective way to achieve this, as currently known, is with the aid of baffles and providing a particular alignment between the illumination source, the object, the baffles, and the imaging system.

In the design of machine vision systems and wafer identification (ID) systems, a designer (e.g., systems engineer) generally makes a number of design compromises. For example, if a lens aperture is made large, a limiting resolution of the system will generally be higher and the system will generally be more efficient. A more efficient system demands less sensitivity or gain from an image sensor, and the system demands less light from an illumination system. If the illumination system demands less light, less demand is placed on a power supply system and less heat is dissipated. Heat dissipation is generally a major hurdle in achieving a design objective of achieving compact packaging.

Conversely, if the system aperture is made small, the limiting resolution of the system is reduced, some aberrations are reduced, a depth of focus is increased, a very significant demand is made upon the image sensor for sensitivity and/or gain, and a very significant demand is placed on the illumination system to provide substantially more light. Demands on the illumination system place demands upon the power supply system and thereby exacerbate problems of thermal dissipation within a compact package.

Heretofore, commercial wafer ID reading systems, including previous generations manufactured by Electro Scientific Industries, Inc. of Portland, Oreg., the assignee of this patent application (e.g., ScribeView™ Models 1 through 5P) and others within the industry (e.g., Cognex Corp. of Natick, Mass., and Kowa Co., LTD. of Tokyo, Japan) have employed optical systems with a working distance range (depth of focus in object space) of approximately ±1 mm or less. Although such systems are workable, they require a user to make adjustments to the focus position of the lens and/or an adjustment to the position of the wafer ID reader to account for even minor changes to the working distance. The working distance may change, for example, if the thickness of the object changes, or if there is imprecision in the robotic system that presents the wafer to the wafer ID reading system.

It would be preferable if the range of working distances for a wafer ID system in a fixed configuration spanned more than approximately ±1 mm. If this range could be extended by an order of magnitude, focusing and setup of the system would be trivial compared to existing systems. For example, current systems generally require mounting and focusing of the system in a powered-up state in accordance with an iterative procedure in which the image can be electronically monitored and a user may make a change in focus adjustment or position while monitoring an electronically presented image. The user generally makes adjustments until a satisfactory image is obtained. If the working distance range could be extended to approximately ±10 mm, the wafer could be mounted while the wafer ID system is in an unpowered state using a simple ruler to determine an appropriate working distance.

Moreover, with existing systems, process variations that cause a change in working distance of approximately 1 mm generally require user intervention to either adjust the process to re-achieve the previous working distance or to adjust the focus of the wafer ID system, for example, by turning a lens-focus barrel or turning a focus-adjustment screw. It would be preferable if minor process variations that resulted in changes in the working distance by just a few millimeters could be accommodated by the wafer ID system with no user intervention.

SUMMARY OF THE DISCLOSURE

The embodiments disclosed herein provide systems and methods for imaging a planar specular object such as a semiconductor wafer. In one embodiment, an imaging system for imaging a defect on a planar specular object includes a telecentric lens having a sufficiently aspherical surface such that the telecentric lens is substantially corrected for an optical aberration. The imaging system also includes a telecentric stop including an aperture therein to block light reflected from the planar specular object while allowing light reflected from the defect to pass through the aperture. The imaging system also includes a second lens group having a system stop positioned between the telecentric stop and the second lens group, the second lens group being substantially corrected for the optical aberration independent of the telecentric lens.

In one embodiment, a telecentric on-axis darkfield (TOAD) lighting device includes a first circular array of illumination sources arranged radially with respect to a center point. The first circular array is located at a first radius from the center point. The TOAD lighting device also includes a second circular array of illumination sources arranged tangentially with respect to the center point. The second circular array is located at a second radius from the center point. In one embodiment, the second radius is longer than the first radius.

In one embodiment, a method is provided for aligning a telecentric on-axis darkfield (TOAD) lighting device with a substantially specular surface. The TOAD lighting device has a plurality of concentric illumination arrays. The method includes adjusting an angle of incidence between the TOAD lighting device and an object plane in a first direction until an area of intense brightness is substantially removed from a first side of an image of the specular surface, and recording the adjusted angle of incidence as a first measurement. The method also includes adjusting the angle of incidence between the TOAD lighting device and the object plane in an opposite direction as compared to the first direction until the area of intense brightness is substantially removed from a second side of the image of the specular surface, and recording the readjusted angle of incidence as a second measurement. The method further includes determining an aligned angle of incidence for the first direction as an approximate difference between the first measurement and the second measurement.

In one embodiment, an imaging system for imaging a semiconductor wafer includes means for illuminating the wafer and means for providing an image of the wafer to a sensing means. A working distance is defined by a distance between the wafer and the means for providing the image to the sensing means. The imaging system further includes means for maintaining focus of the image when the working distance changes over a range of approximately ±10 mm.

Additional aspects and advantages will be apparent from the following detailed description, which proceeds with reference to the accompanying drawings.

DETAILED DESCRIPTION OF PREFERRED EMBODIMENTS

Figures 1A, 1B:
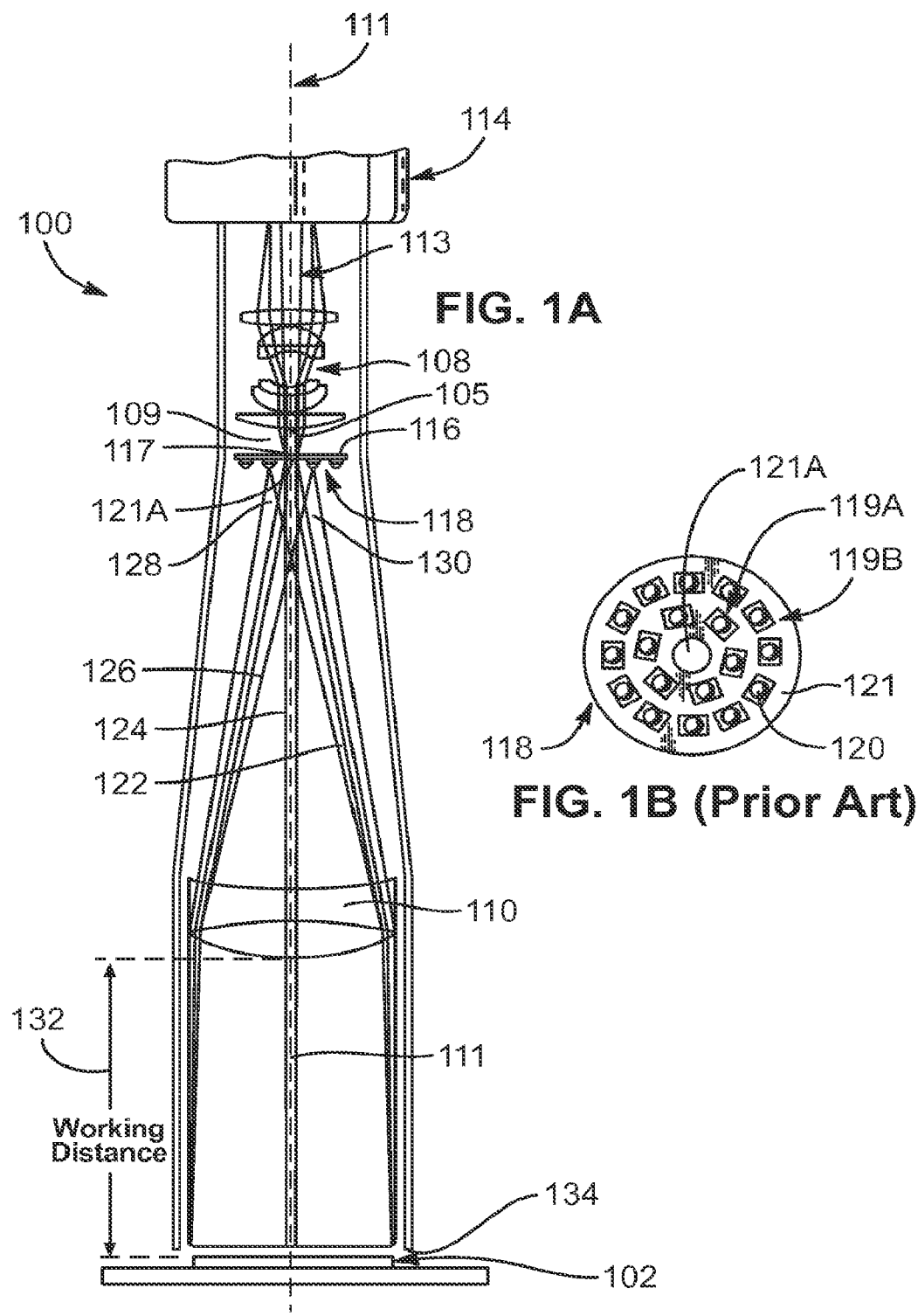
FIG. 1A is a partially pictorial, partially sectional diagram of an optical imaging system for imaging a planar object.
FIG. 1B is a plan view of a prior art illumination source usable by the optical imaging system shown in FIG. 1A.

Systems and methods are provided for illuminating and forming an image of a predominantly planar and specular surface such that deviations from planarity or specularity of the surface being imaged are reproduced with enhanced contrast. According to one embodiment, an increased working distance range is provided to account for variations in the surface being imaged and/or variations in a distance between the surface and an identification (ID) system.

In addition, or in another embodiment, concentric circular arrays of illumination sources are arranged for increased illumination without increasing the diameters of the respective arrays. In one embodiment, a method is provided for aligning concentric illumination arrays with a surface to be imaged so as to reduce the angle of incidence. In addition, or in other embodiments, a system includes a front lens and a rear lens group that are independently well corrected for perturbations such that the magnification of the system can be changed without changing both the front lens and the rear lens group.

The embodiments described herein utilize a telecentric lens to illuminate objects with symmetric coaxial narrow angle dark field illumination. This illumination technique is particularly suited to highlighting minor features or defects on planar specular objects. Specific examples of such objects include silicon wafers. The defects may include soft mark symbols on silicon wafers and/or edge irregularities on chip scale devices.

A light source provides annular cones of light rays toward a telecentric lens. The telecentric lens redirects the light rays toward a substantially planar and specular object such that the light rays are parallel and normal to the object. A property of the planar specular object is to reflect light at an angle complementary to the incident angle. Thus, in this case, the light is reflected normal to the surface of the object. Upon reflection, the light rays are referred to herein as image rays. The image rays are retroreflected from a substantially planar specular object and inversely transformed through the telecentric lens to the point at which they originated.

The system provides a telecentric stop, with a central aperture coincident with the light source such that substantially no light passes through to a camera. However, if there is a defect in the specular surface, the light will be disturbed and it is probable that some portion of the light will pass through the aperture of the telecentric stop and onto a camera.

Reference is now made to the figures in which like reference numerals refer to like elements. For clarity, the first digit of a reference numeral indicates the figure number in which the corresponding element is first used. In the following description, numerous specific details are provided for a thorough understanding of the embodiments disclosed herein. However, those skilled in the art will recognize that the embodiments can be practiced without one or more of the specific details, or with other methods, components, or materials. Further, in some cases, well-known structures, materials, or operations are not shown or described in detail in order to avoid obscuring aspects of the embodiments. Furthermore, the described features, structures, or characteristics may be combined in any suitable manner in one or more embodiments.

A wafer ID system is described in U.S. Pat. No. 6,870,949 (hereinafter, "the '949 patent"). Certain embodiments discussed herein modify the '949 patent to include additional features that greatly expand (e.g., by approximately ten times) the working distance range for a fixed configuration without necessitating physical or optical adjustments and that simplify changing the magnification of the system. For purposes of discussion, FIGS. 3 and 5 of the '949 patent are shown and discussed as FIGS. 1A and 1B herein, respectively.

FIG. 1A is a partially pictorial, partially sectional diagram of an optical imaging system 100 for imaging a planar object 102. The planar object 102 may comprise, for example, a silicon wafer that is specular in nature. Silicon wafers generally include defects such as a soft marks (not shown). As is known in the art, a soft mark is made up of a collection of laser etched pits and provides information regarding a particular silicon wafer on which it is etched. Silicon wafers also generally include a plurality of semiconductor devices. While the present disclosure is described in terms of inspecting silicon wafers and, in particular, imaging soft marks, it is understood that the present disclosure has equal applicability to imaging other planar objects. For example, when semiconductor devices are singulated, they may be inspected according to certain embodiments disclosed herein for edge defects.

The optical imaging system 100 shown in FIG. 1A includes a pair of lens groups referred to herein as a rear group 108 and a telecentric field lens 110. One source of appropriate lenses for both rear lens group 108 and telecentric field lens 110 is Edmund Optics Inc. of Barrington, N.J. The rear lens group 108 and the telecentric field lens 110 operate together to direct to a camera 114 an image 113 of a defect such as a softmark, as will be described in greater detail below. The camera 114 is preferably a digital camera including a charge coupled device (CCD) or a complementary metal-oxide semiconductor (CMOS) type sensor.

The rear lens group 108 is defined by a collection of corrected objective lenses and includes an entrance pupil 109. The rear lens group 108 is preferably low in distortion and has sufficient resolving power to complement the camera 114. It is understood that the rear lens group 108 may be different depending upon what type of camera 114 is used. As discussed below, in one embodiment disclosed herein, the rear lens group 108 and the telecentric field lens 110 are each independently well corrected for aberrations such that either one can be replaced without affecting the performance of the other.

It is understood that the telecentric field lens 110 operates as a telecentric field lens to render the imaging of the object telecentric along the plane of the object 102. Put another way, light rays are parallel to one another as they exit the telecentric lens 110 and are preferably normal to the plane of the object 102. When illuminated by a light source 118, it is understood that the telecentric lens 110 and the lens group 108 operate to form the image 113 at the camera 114. The telecentric lens 110 has a number of defining characteristics including an axis 111 and a telecentric aperture or focal point. As illustrated in FIG. 1A, the focal point of the telecentric field lens 110 is coincident with the entrance pupil 109 of the rear lens group 108. The axis 111 defines the optical axis for system 100 such that the rear lens 108 and the camera 114 are similarly positioned along the axis 111.

The light source 118 is positioned to provide narrow angle lighting that is coaxial with the axis 111 of the telecentric field lens 110. FIG. 1A illustrates one positioning of the light source 118 physically along the axis 111. However, as disclosed in the '949 patent, it is understood that the light source 118 can be positioned physically remote from the axis 111 in an optically equivalent manner. For example, FIG. 6 of the '949 patent illustrates a different position of the light source 118 that is optically equivalent to the embodiment shown in FIG. 1A herein. Optical equivalence is achieved using a partially reflective mirror or beam splitter (not shown) positioned along the axis 111 of the telecentric field lens 110. The beam splitter allows the light source 118 to be positioned normal to the axis 111 of the telecentric field lens 110.

A telecentric stop 116 is positioned between the rear lens group 108 and the telecentric field lens 110. The telecentric stop 116 is centered on the axis 111 of the telecentric field lens 110. The telecentric stop 116 is preferably placed proximate the entrance pupil 109 of the rear lens group 108. The rear lens group 108 has a system stop 105 positioned between the telecentric stop 116 and the rear lens group 108. The telecentric stop 116 is preferably a physical optical stop which includes a central aperture 117. The aperture 117 is also positioned proximate to the focal point of telecentric lens 110.

FIG. 1B is a plan view of an illumination source 118 usable by the optical imaging system shown in FIG. 1A. The illumination source illustrated in FIG. 1B comprises an annular light source utilizing a plurality of light emitting diodes (LEDs) 120 mounted to a printed circuit board 121. It is understood that in one embodiment the printed circuit board 121 may function as the telecentric stop 116. The printed circuit board 121 includes an aperture 121A which is at least as large as the aperture 117 of telecentric stop 116.

In the event that an iris diaphragm aperture is used together with the telecentric stop 116, the aperture 121A is at least as large as the largest aperture setting available. As shown, the LEDs 120 are organized into an inner circular group 119A and an outer circular group 119B. It is understood that the inner group 119A and the outer group 119B provide slightly different narrow angle lighting of the object 102. The inner group 119A and the outer group 119B may be illuminated simultaneously or alternately, depending upon the qualities of the object 102. It is understood that additional circular groups of the LEDs 120 could be provided.

The sensitivity of the optical imaging system 100 to a type of defect is principally determined by the focal ratio between the telecentric lens 110 and the diameter of the light source 118. This sensitivity may be adjusted, for example, selecting between the different diameters of the inner group 119A and the outer group 119B of the light source 118. Alternatively, this sensitivity may be adjusted by selectively adjusting the diameter of the aperture 117 of the telecentric stop 116. The aperture 117 may be adjustable through the use of an iris diaphragm to provide an adjustable focal ratio for the system 100.

In operation, the light source 118 causes light rays 128, 130 to project toward telecentric field lens 110 such that the rays 128, 130 are focused proximate to the object 102 and are substantially parallel to one another. It is understood that the light rays 128, 130 are projected as annular cones which become parallel as they pass through the telecentric lens 110. The light rays 128, 130 are reflected from the object 102 as image forming rays 122, 124, 126. In the event that the light rays 128, 130 reflect from a specular portion of the object 102, the image forming rays 122, 126 will strike the telecentric stop 116 and not enter the rear lens group 108. In particular, the image rays 122, 126 are retro-reflected from a substantially planar and specular surface to create annular cones of illumination which return to their point of origin as a mirror image. However, when a portion of the light rays 128, 130 is reflected from a defect, the image forming rays 124 pass through the aperture 117 in the telecentric stop 116 where they are focused by the rear lens group 108 and form an image 113 at the camera 114.

The optical imaging system 100 allows the angle between the optical axis 111 and the narrow angle dark field lighting to be adjusted so as to be arbitrarily small to the point of becoming bright field lighting, if desired. Further, the sensitivity of the system 100 can be adjusted by selecting a different diameter of lighting or by adjusting the aperture 117 of the telecentric stop 116. Further, the full field of view of the camera 114 can be used, and the system 100 provides full circular symmetry over the entire field of view.

A. Increasing the Depth of Focus

As discussed above, the embodiments disclosed herein expand the working distance range for a fixed configuration of the optical imaging system 100 without necessitating physical or optical adjustments. In general, the degree of mis-focus of a camera system at the image plane can be described by the equation $$\varphi = \frac{\pi A^2}{4\lambda}\left(\frac{1}{f} - \frac{1}{s_o} - \frac{1}{s_i}\right),$$

where $\phi$ is the defocus, A is the linear dimension of the aperture, $\lambda$ is the wavelength of light, f is the focal length of the lens, and s is the distance from the lens to the object plane ($s_o$) and the image plane ($s_i$) respectively, as indicated by subscript.

Grouping the variables that are fixed for the system into the constants x and y, simplifies this equation to:

$$\varphi = xA^2\left(y - \frac{1}{s_o}\right).$$

The dominant factor is the size of the aperture and, of course, the deviation in $s_o$. Note that for a system in focus, $y=1/s_o$ and $\phi$ becomes zero. The above equation relates the aperture and the working distance deviation to a defocus in the image plane. This can be related to a defocus in the object plane, $\omega$, by multiplying by the system magnification m squared:

$$\omega = \phi m^2.$$

For a given field of view, the system magnification m is determined by the size (also known as the format) of the sensor. The smaller the sensor, the smaller the system magnification m, and the smaller the defocus parameter for a given variation in working distance.

One solution is to select a very small aperture (so that $A^2$ is a very small number) and a very small imager (so that $m^2$ is a very small number), thereby minimizing the product $A^2 m^2$ and minimizing defocus for a given variation in object distance. However, the power efficiency of the system relates to the aperture. In a simplified form, the efficiency T of an optical system in focusing a portion of the radiant energy that illuminated the object can be related to radiant energy that is incident upon the imaging sensor at the focal plane to the linear dimension of the aperture squared, e.g., $$T \approx A^2.$$

Thus, arbitrarily reducing A to increase the depth of focus (and hence the range of working distance) diminishes the efficiency of the optical system to transmit optical power to the point that the image will be too dark to recover useful information therefrom.

FIG. 1A illustrates a working distance 132 between a top surface of the planar object 102 and a front surface of the telecentric field lens 110. An artisan will recognize from the disclosure herein that the working distance 132 may alternatively be defined as a distance between the top surface of the planar object 102 and, for example, a bottom of an exterior enclosure 134 of the optical imaging system 100. The depth of focus in the object space of the optical imaging system 100 is the range of distances that the working distance 132 can vary (e.g., the working distance range) such that the image 113 is still in substantial focus for the camera 114.

A larger working distance range allows for thickness variations in the planar object 102 or between successive planar objects without the need to refocus the optical imaging system. Further, a larger working distance range allows a user to estimate (e.g., by a simple ruler measurement or by eye) a proper working distance 132 to maintain substantial focus.

In one embodiment disclosed herein, the working distance range is approximately ±10 mm. According to one such embodiment, the imaging surface of the camera 114 is selected to be relatively small so as to decrease the system magnification m. In one embodiment, the length and width of the imaging surface are each selected to be in a range between approximately 2.5 mm and approximately 5.5 mm. In an example embodiment, the imaging surface is approximately 4.51 mm long by approximately 2.88 mm wide. By way of comparison, a standard imager (e.g., an imager in the ScribeRead 5P imaging system available from Electro Scientific Industries of Portland, Oreg.) is approximately 6.4 mm long by approximately 4.8 mm wide.

In addition, the camera 114 is selected so as to have a relatively high sensitivity. Thus, the impact of reducing the system efficiency T is reduced or minimized. Such a sensor that is suitable to use as the camera 114 is manufactured, for example, by Micron and uses a CMOS as compared to the more conventional CCD imager. In an example embodiment, the camera 114 includes model MT9V022 from Micron Imaging of Boise, Id. and has a sensitivity of approximately 2.0V/lux-sec at a wavelength of approximately 550 nm. Here, V is volts, and lux-sec is an intensity-time product. An artisan will recognize that green light has a wavelength of approximately 550 nm, and that the sensitivity may be somewhat less at other visible wavelengths.

To achieve the working distance range of approximately ±10 mm, according to one embodiment, the illumination source 118 is configured to provide a large quantity of light. The LEDs 120 are selected to provide a very high brightness. In an example embodiment, the LEDs 120 include model SML-LX0402SIC from Lumex Inc. of Palatin, Ill. and has a brightness of approximately 140 mcd (millicandela) at approximately 20 mA. In one embodiment, the LEDs 120 are lensed to capture and use as much of the energy as possible. In addition, or in another embodiment, the LEDs 120 are pulsed with a very high current to achieve high brightness levels. Techniques for achieving high brightness illumination are described below.

In one embodiment, selecting a small imaging surface for the camera 114, selecting the camera 114 to have a high sensitivity, and selecting very high brightness LEDs 120, as discussed above, provides an optical system with a focal ratio of f/12 as compared to the usual f/5.8, and a small system magnification of approximately 0.14×. Note that an f/12 system passes less than one-quarter of the energy as compared with that of an f/5.8 system, requiring that the balance of the optical imaging system 100 to be four times more powerful and/or more efficient.

B. Arranging Lighting Packages

Telecentric on-axis darkfield (TOAD) lighting, being a darkfield lighting method, is a relatively inefficient lighting method because a small percentage of light reflecting off the object 102 is captured as compared to the amount of light transmitted to illuminate the object 102. Thus, a large quantity of light is required to be transmitted to the object 102 to offset the losses inherent in the darkfield lighting method.

Size constraints imposed by industry in machine vision applications significantly decrease the amount of room available for darkfield lighting sources. A small lighting source package, as well as a high density arrangement of the light sources, would be beneficial. As shown in FIG. 1B, the TOAD lighting scenario described in the '949 patent uses an array of illumination (inner group 119A, outer group 119B, or both). As the distance from the center of the array to the edge of the array decreases, the ability to perceive soft and super-soft wafer marks increases. Thus, it is advantageous to make this distance as small as possible. Further, as the distance decreases, the space used by the illumination source 118 decreases significantly.

Providing multiple illumination arrays at multiple center-to-edge distances is also beneficial, and provides for differing manners of object illumination and differing degrees of super-soft, soft, and hard wafer mark detection. For this reason, multiple lighting arrays are helpful. However, as discussed below, multiple lighting arrays lead to packaging issues. The packaging issues are solved, according to one embodiment disclosed herein, by using small individual illumination sources and arranging the illumination sources into arrays in which the density of the sources, as well as the density of the arrays, is increased or maximized.

Figure 2:
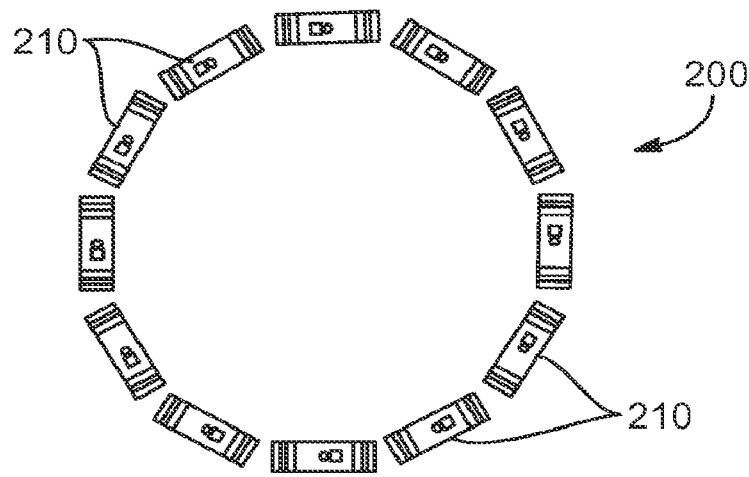
FIG. 2 is a schematic diagram of a conventional annular illumination array including a plurality of illumination sources 210.

FIG. 2 is a schematic diagram of a conventional annular illumination array 200 including a plurality of illumination sources 210 (twelve shown). The illumination sources 210 in this example are rectangular and may comprise, for example, LEDs. The illumination sources 210 are tangentially arranged in a circular pattern. An artisan will recognize that the arrangement of the annular illumination array 200 can be changed by adding or removing illumination sources 210, and by increasing or decreasing the radius of the annular illumination array 200. For example, to decrease the radius of the annular illumination array 200, one or more of the illumination elements 210 would be removed. The remaining illumination elements 210 are rearranged so as to have substantially equal end-to-end spacing in a circular pattern. Removing the one or more illumination sources 210 to decrease the radius decreases the brightness level of the array 200.

Figure 3:
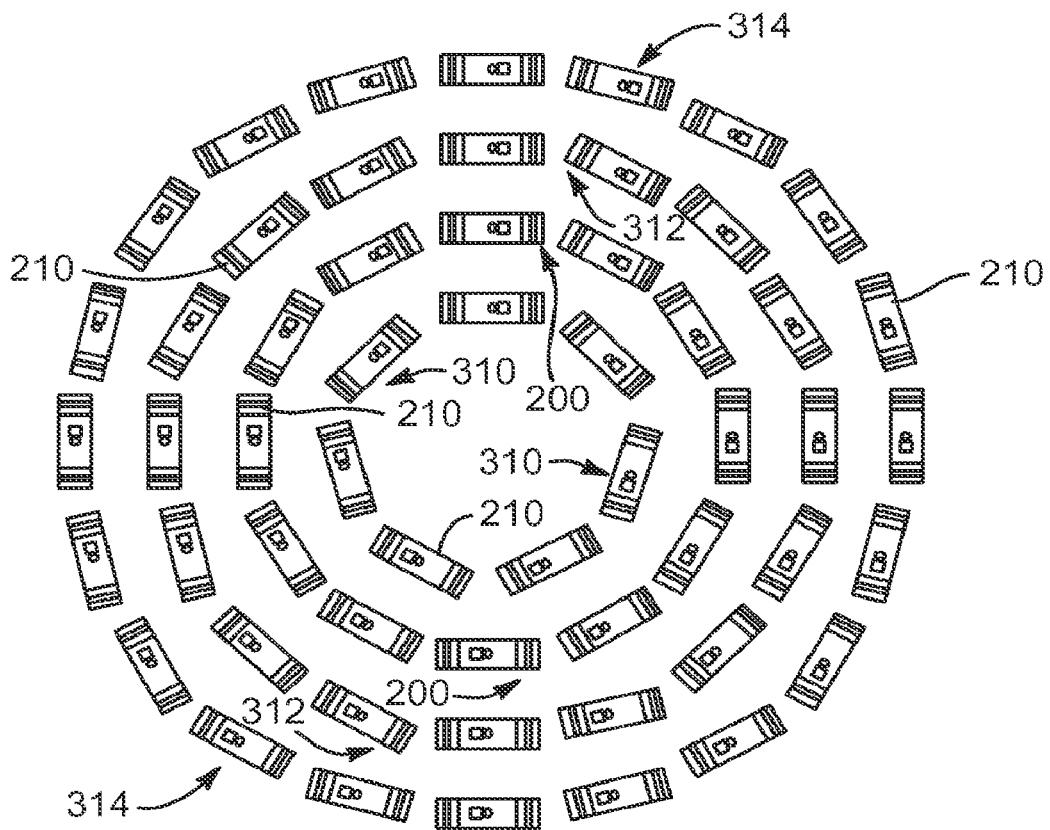
FIG. 3 is a schematic diagram of a conventional arrangement of the annular illumination array shown in FIG. 2 concentrically located with three other annular illumination arrays.

The annular illumination array 200 can be concentrically located with other arrays that can be separately turned on and off. For example, FIG. 3 is a schematic diagram of a conventional arrangement of the annular illumination array 200 shown in FIG. 2 concentrically located with three other annular illumination arrays 310, 312, 314. Each of the annular illumination arrays 310, 200, 312, 314 has a different radius and a different number of tangentially arranged illumination sources 210. It may be desirable, though not required, to maintain brightness levels between the individual arrays 310, 200, 312, 314. Because of R-squared losses, the number of illumination sources 210 in each array 310, 200, 312, 314 is increased from the previous inner array, when possible. In this example, the annular illumination arrays 310, 200, 312, 314 include seven, twelve, sixteen and twenty illumination sources 210, respectively.

Figure 4:
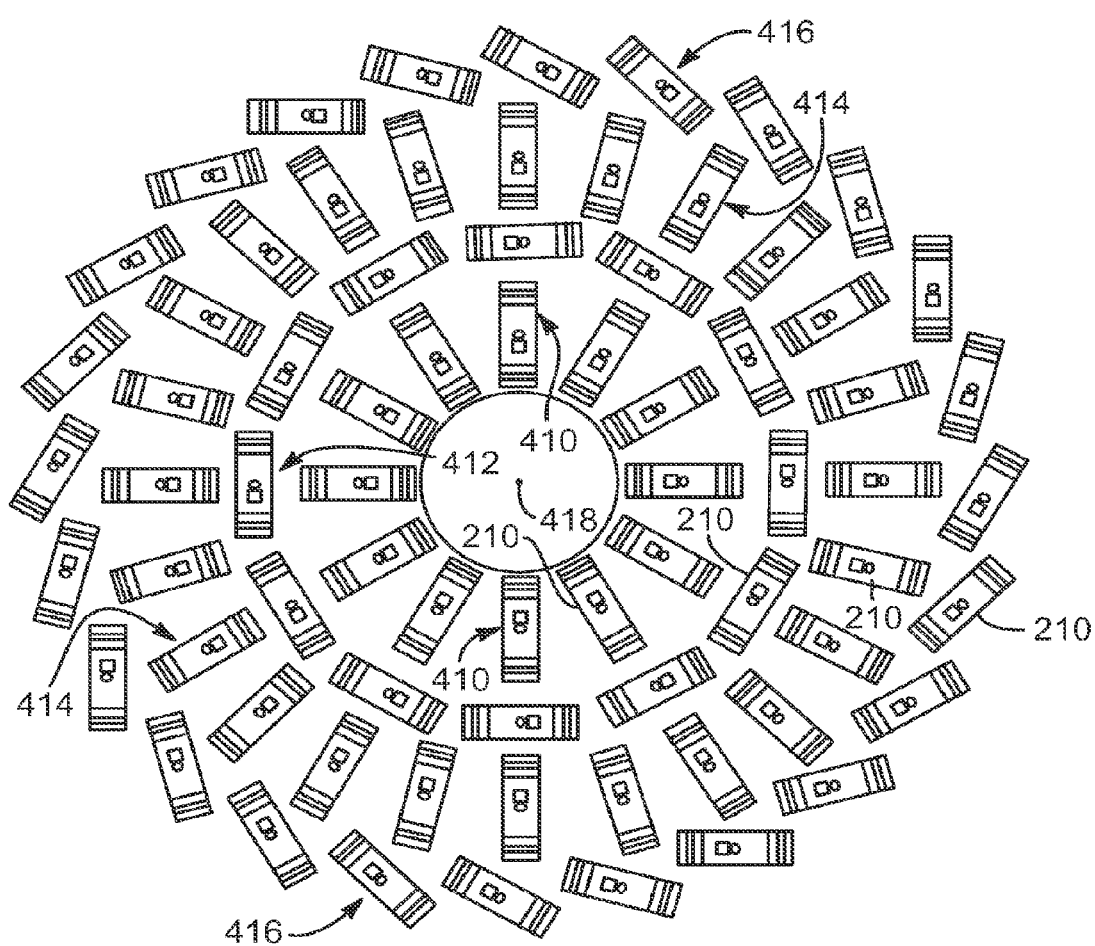
FIG. 4 is a schematic diagram of a plurality of concentrically located illumination arrays arranged according to one embodiment.

As shown in FIG. 3, under conventional illumination source layouts, each array is oriented in a similar manner (e.g., tangentially around a common center point). However, in one embodiment disclosed herein, the conventional arrangement is improved by increasing the number of illumination sources in each array. FIG. 4 is a schematic diagram of a plurality of concentrically located illumination arrays 410, 412, 414, 416 arranged according to one embodiment. Each of the illumination arrays 410, 412, 414, 416 has a plurality of illumination sources 210 arranged in a circular pattern around a common center 418.

A comparison between the arrangements shown in FIGS. 3 and 4 reveals a significant increase in the number of illumination sources 210 used in the arrays 410, 414, 416. Thus, the arrays 410, 414, 416 provide a significant increase in the amount of luminescence provided as compared to the arrays 310, 312, 314, respectively.

The innermost illumination array 410 shown in FIG. 4 includes twelve illumination sources 210 radially arranged in a circular pattern. A radius from the common center 418 to an approximate center of the illumination sources 210 in the array 410 is approximately equal to a radius of the innermost array 310 shown in FIG. 3. However, the innermost array 310 shown in FIG. 3 has seven illumination sources 210 as compared to the twelve illumination sources 210 in the array 410.

The next innermost array 412 shown in FIG. 4 includes twelve illumination sources 210 tangentially arranged in a circular pattern. The radius and number of illumination sources 210 in the array 412 is substantially the same as the radius and number of illumination sources 210 in the array 200 shown in FIG. 3.

The next innermost array 414 shown in FIG. 4 includes twenty-four illumination sources 210 radially arranged in a circular pattern. A radius from the common center 418 to an approximate center of the illumination sources 210 in the array 414 is approximately equal to a radius of the array 312 shown in FIG. 3. However, the array 312 shown in FIG. 3 has sixteen illumination sources 210 as compared to the twenty-four illumination sources 210 in the array 414.

The outermost array 416 shown in FIG. 4 includes twenty-four illumination sources 210 arranged in a circular pattern. To achieve a desired separation between the ends of the illumination sources 210 in the array 416, the illumination sources 210 are offset from a tangential configuration. In another embodiment, to achieve the desired separation, one or more of the illumination sources 210 is removed from the array 416 and the remaining illumination sources 210 are arranged in a substantially tangential configuration. As shown in FIG. 4, a radius from the common center 418 to an approximate center of the illumination sources 210 in the outermost array 416 is approximately equal to a radius of the outermost array 314 shown in FIG. 3. However, the array 314 shown in FIG. 3 has twenty illumination sources 210 as compared to the twenty-four illumination sources 210 in the array 414.

Figure 5:
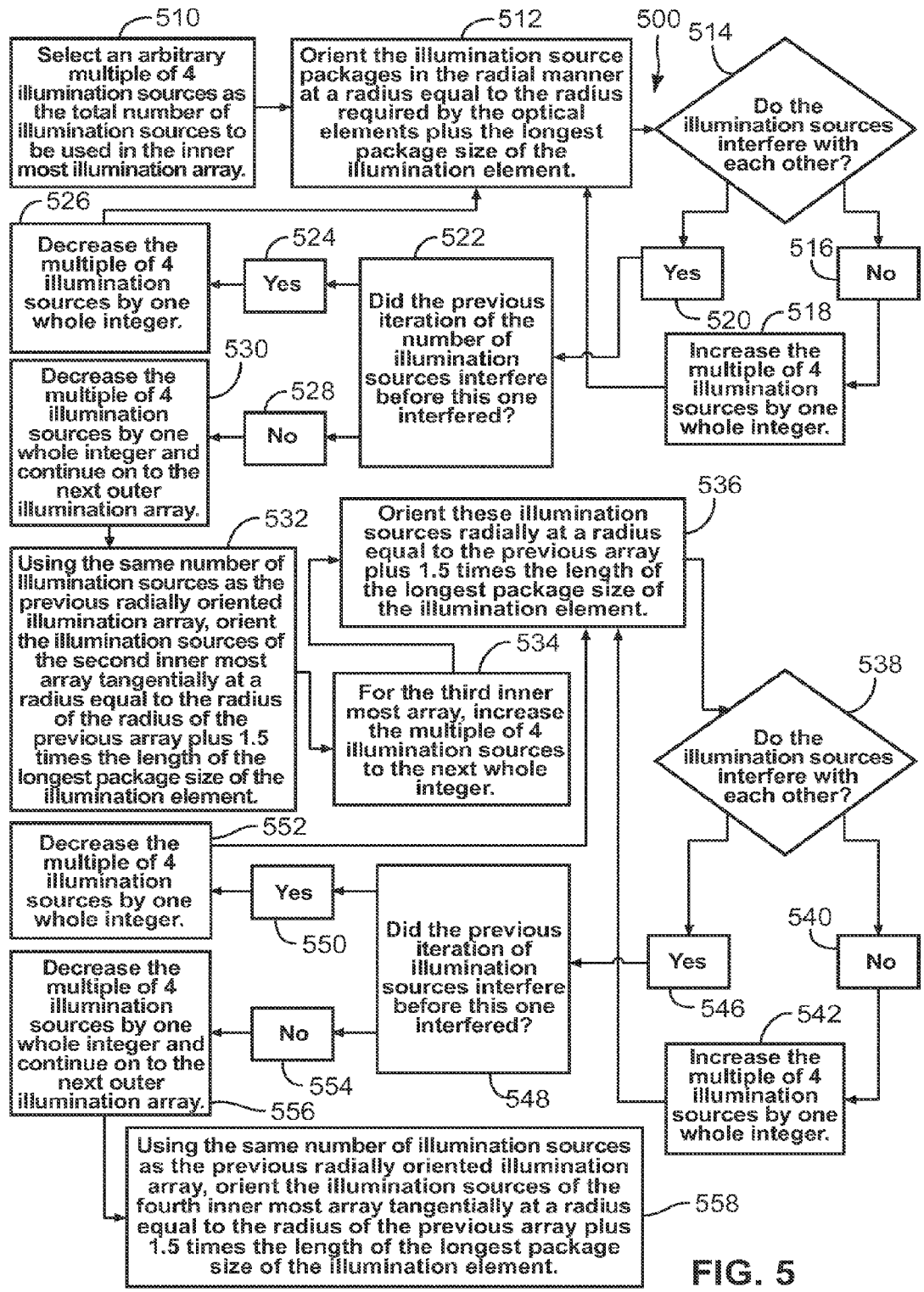
FIG. 5 is a flowchart illustrating a process for arranging a high density illumination array according to one embodiment.

FIG. 5 is a flowchart illustrating a process 500 for arranging a high density illumination array according to one embodiment. The process 500 may be used, for example, to layout the arrangement of illumination array 410, 412, 414, 416 schematically illustrated in FIG. 4. At a step 510, the process 500 includes selecting an arbitrary multiple of four illumination sources as a total number of illumination sources to be used in an innermost illumination array. An artisan will recognize from the disclosure herein that initially selecting a multiple of four illumination sources may be arbitrary or may be chosen for electrical circuitry reasons (e.g., to achieve balanced drivers). However, any number of illumination sources may be initially selected.

At a step 512, the process 500 includes orienting the selected illumination sources in a radial manner at a radius equal to the radius desired or required for use by optical elements of an optical imaging system (e.g., the optical imaging system 100 discussed above with respect to FIG. 1) plus a longest package size of the illumination elements (e.g., the length of the illumination sources 210 shown in FIG. 4).

At a step 514, the process 500 queries whether the illumination sources interfere with each other. If the physical layout of the illumination sources is such that they do not touch one another or that they do have a desired spacing, the process 500 passes through a no path 516 to a step 518 where the process 500 increases the multiple of four illumination sources by one whole integer. The process then returns to the step 512 followed by step 514. If the illumination sources do interfere with each other, the process 500 proceeds from the step 514 through a yes path 520 to a step 522 where the process 500 queries whether the previous iteration of the number of illumination sources interfered before the current number of illumination sources interfered.

If the previous iteration also interfered, the process 500 passes through a yes path 524 to a step 526 where the multiple of four illumination sources is decreased by one whole integer. From the step 526, the process 500 returns to the step 512. If the previous iteration of the number of illumination sources did not interfere, the process 500 passes through a no path 528 to a step 530 where the multiple of four illumination sources is decreased by one whole integer and the process 500 continues on to the next outer illumination array. At this point in the process 500, the innermost illumination array is complete. For example, the innermost illumination array 410 shown in FIG. 4 with radially arranged illumination sources 210 may have been configured according to the process 500 discussed above.

At a step 532, using the same number of illumination sources as the previous radially oriented illumination array, the process 500 orients the illumination sources of a second innermost array tangentially at a radius equal to the radius of the previous array plus 1.5 times the length of the longest package size of the illumination elements. An artisan will recognize from the disclosure herein that a different radius for the second innermost array may be selected in other embodiments. At this point in the process 500, the second innermost illumination array is complete. For example, the second innermost illumination array 412 shown in FIG. 4 may have been configured according to the process 500 discussed above. Although not shown in FIG. 4 or 5, if the illumination sources 210 in the second innermost illumination array 412 interfere with each other, they may be offset from the tangential orientation similar to the orientation of the outermost array 416.

At a step 534, for a third innermost array, the process 500 increases the multiple of four illumination sources to the next whole integer. At a step 536, the process 500 orients these illumination sources for the third innermost array in a radial configuration at a radius equal to the previous array plus 1.5 times the length of the longest package size of the illumination elements.

In an example embodiment, the illumination sources are arranged in four circular arrays similar to the arrays 410, 412, 414, 416 shown in FIG. 4, where a first circular array has a radius of approximately 2.2 mm, a second circular array has a radius of approximately 3.8 mm, a third circular array has a radius of approximately 5.2 mm, and a fourth circular array has a radius of approximately 6.6 mm. In such an embodiment, each illumination source (e.g., LED package) is approximately 1.2 mm long by approximately 0.6 mm wide and is known in the trade as an 0402 package after the dimensions in inches (0.04"×0.02").

At a step 538, the process 500 queries whether the illumination sources in the third innermost array interfere with each other. If the physical layout of the illumination sources is such that they do not touch one another or that they do have a desired spacing, the process 500 passes through a no path 540 to a step 542 where the process 500 increases the multiple of four illumination sources by one whole integer. The process then returns to the step 536 followed by step 538. If the illumination sources do interfere with each other, the process 500 proceeds from the step 538 through a yes path 546 to a step 548 where the process 500 queries whether the previous iteration of the number of illumination sources interfered before the current number of illumination sources interfered.

If the previous iteration also interfered, the process 500 passes through a yes path 550 to a step 552 where the multiple of four illumination sources is decreased by one whole integer. From the step 552, the process 500 returns to the step 536. If the previous iteration of the number of illumination sources did not interfere, the process 500 passes through a no path 554 to a step 556 where the multiple of four illumination sources is decreased by one whole integer and the process 500 continues on to the next outer illumination array. At this point in the process 500, the third innermost illumination array is complete. For example, the third innermost illumination array 414 shown in FIG. 4 with radially arranged illumination sources 210 may have been configured according to the process 500 discussed above.

At a step 558, using the same number of illumination sources as the previous radially oriented illumination array, the process 500 orients the illumination sources of a fourth innermost array tangentially at a radius equal to the radius of the previous array plus 1.5 times the length of the longest package size of the illumination elements. At this point in the process 500, the fourth innermost illumination array is complete. For example, the fourth innermost illumination array 416 shown in FIG. 4 may have been configured according to the process 500 discussed above. As discussed above, if the illumination sources 210 in the fourth innermost illumination array 416 interfere with each other, they may be offset from the tangential orientation, as shown in FIG. 4.

An artisan will recognize from the disclosure herein that the process 500 may continue in like manner, alternating between radially oriented illumination arrays and tangentially oriented illumination arrays (or offset from tangential to provide desired spacing), to create any number of illumination arrays. Further, the order may be reversed such that the innermost array has a tangential arrangement of illumination sources, the second innermost array has a radial arrangement of illumination sources, and so forth. In addition, the radius of each array may be selected to be any desired length.

C. Aligning TOAD Lighting Arrays

Telecentric on-axis darkfield (TOAD) lighting, being a darkfield lighting method, relies on the angle of incidence between the illumination source and the object being illuminated. As the darkfield angle from the optical axis becomes smaller, and softer marks can be perceived, the sensitivity to perturbations in alignment increases. The alignment requirements for wafer ID systems that use very narrow angle darkfield lighting, such as TOAD lighting, therefore become increasingly more critical. A relatively simple and convenient method for alignment according to one embodiment is described below.

Because of the layout and design of the optical imaging system 100 shown in FIG. 1A (also referred to herein as the reader unit 100), aligning the reader unit 100 to one or more TOAD lighting arrays will consequently align the reader unit 100 to all of the arrays as a consequence of their concentricity. The TOAD lighting arrays include, for example, the illumination arrays 410, 412, 414, 416 shown in FIG. 4. However, other TOAD lighting array arrangements, such as those shown in FIGS. 1B and 2-3, may also be used. An alignment method according to one embodiment includes aligning an innermost array because it will show any misalignment characteristics at smaller misalignment angles than would the other arrays. Thus, aligning the innermost array guarantees the alignment of the optics path in relation to the other TOAD lighting arrays.

Figure 6:
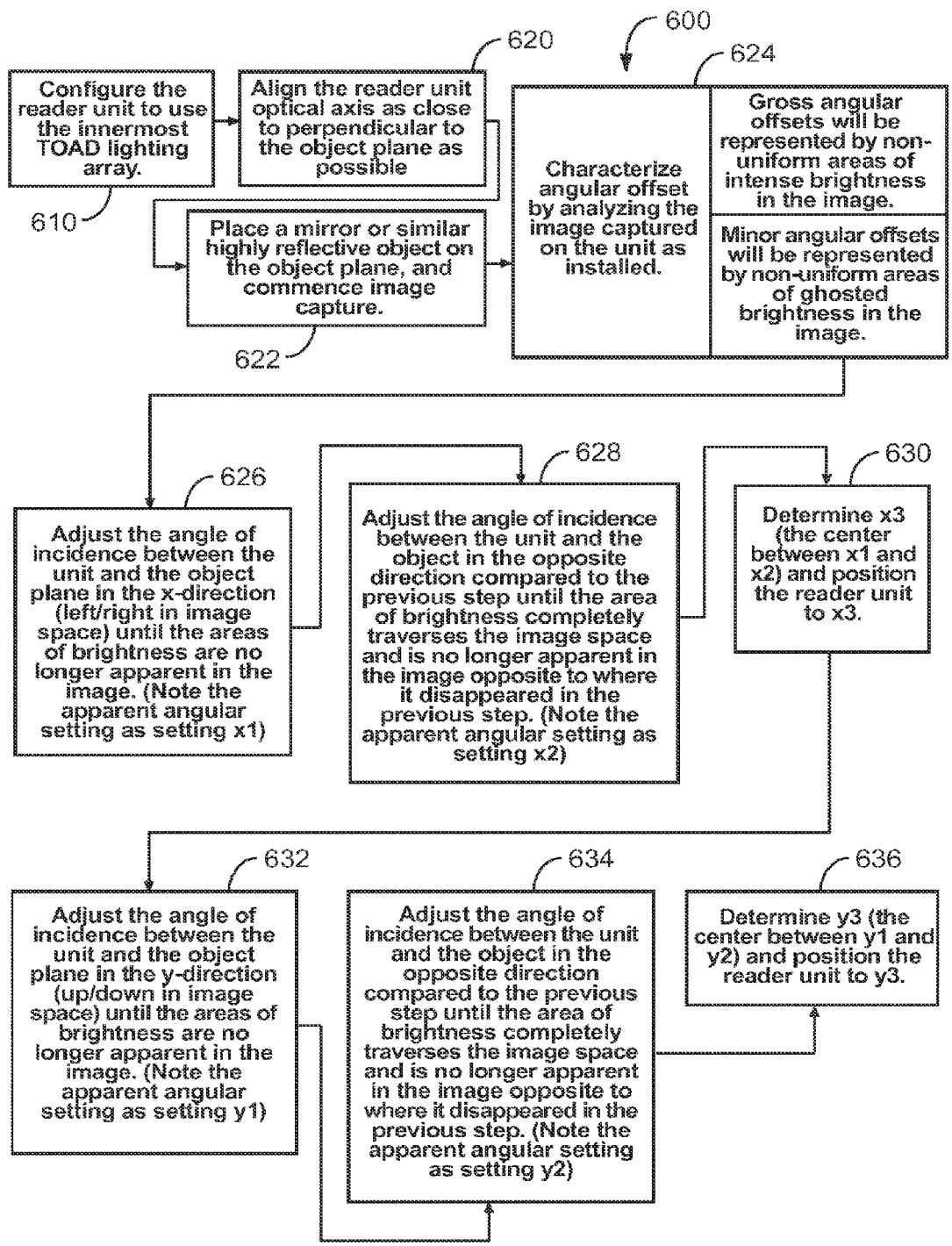
FIG. 6 is a flowchart illustrating a process for aligning telecentric on-axis darkfield (TOAD) lighting arrays according to one embodiment.

FIG. 6 is a flowchart illustrating a process 600 for aligning TOAD lighting arrays according to one embodiment. At a step 610, the process 600 includes configuring a reader unit to use an innermost TOAD lighting array. For example, the optical imaging system 100 may be configured to use the illumination array 410 shown in FIG. 4. At a step 620, the process 600 includes aligning the reader unit optical axis as close to perpendicular to the object plane as possible. At a step 622, a mirror or similar highly reflective object is placed on the object plane, and an image capture process is commenced.

Figure 7A:
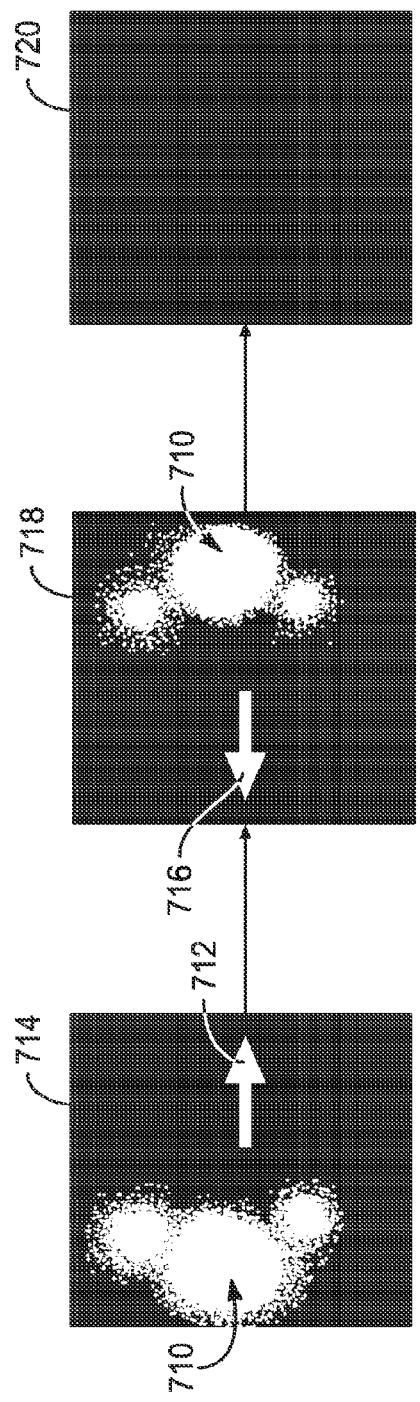
FIGS. 7A and 7B illustrate photographs of a mirror captured on a reader unit according to one embodiment.
Figure 7B:
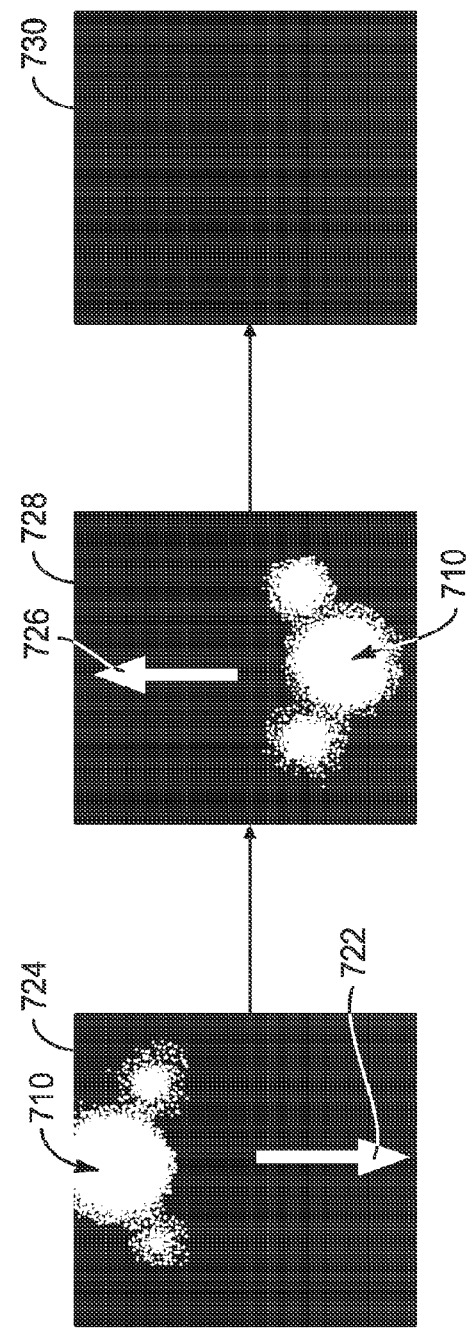

At a step 624, the process 600 includes characterizing angular offset by analyzing the image captured on the reader unit as installed. A gross angular offset is represented by non-uniform areas of intense brightness in the image. Minor angular offsets are represented by areas of ghosted brightness in the image. For example, FIGS. 7A and 7B illustrate photographs of the mirror captured on the reader unit according to one embodiment. The images include areas brightness 710 (e.g., one large and two small areas of intense brightness surrounded by areas of ghosted brightness).

At a step 626, the process 600 includes adjusting the angle of incidence between the reader unit and the object plane in the x-direction (e.g., left/right in image space) until the areas of brightness 710 are no longer apparent in the image. The apparent angular setting is then noted as setting x1. For example, the angle of incidence is adjusted in the direction of an arrow 712 shown in a first image 714 in FIG. 7A. As soon as the areas of brightness 710 move off to the left of the first image 714 and disappear, x1 is recorded.

At a step 628, the process includes adjusting the angle of incidence between the reader unit and the object plane in the opposite direction compared to that of the previous step until the areas of brightness 710 completely traverse the image space and are no longer apparent in the image opposite to where they disappeared in the previous step. The apparent angular setting is then noted as setting x2. For example, the angle of incidence is adjusted in the direction of an arrow 716 shown in a second image 718 in FIG. 7A. As soon as the areas of brightness 710 move off to the right of the second image 718 and disappear, x2 is recorded.

At a step 630, the process 600 includes calculating x3 as an angular setting approximately half way between setting x1 and setting x2. The reader unit is then positioned such that the angle of incidence between the reader unit and the object plane is at setting x3. For example, a third image 720 shown in FIG. 7A illustrates that when the angle of incidence is set at the setting x3, the areas of brightness 710 are not imaged and the TOAD lighting arrays are aligned for the x-direction.

At a step 632, the process 600 includes adjusting the angle of incidence between the reader unit and the object plane in the y-direction (e.g., up/down in image space) until the areas of brightness 710 are no longer apparent in the image. The apparent angular setting is then noted as setting y1. For example, the angle of incidence is adjusted in the direction of an arrow 722 shown in a fourth image 724 in FIG. 7B. As soon as the areas of brightness 710 move off to the top of the fourth image 724 and disappear, y1 is recorded.

At a step 634, the process includes adjusting the angle of incidence between the reader unit and the object plane in the opposite direction compared to the previous step until the areas of brightness 710 completely traverse the image space and are no longer apparent in the image opposite to where they disappeared in the previous step. The apparent angular setting is then noted as setting y2. For example, the angle of incidence is adjusted in the direction of an arrow 726 shown in a fifth image 728 in FIG. 7B. As soon as the areas of brightness 710 move off to the bottom of the fifth image 728 and disappear, y2 is recorded.

At a step 636, the process 600 includes calculating y3 as an angular setting approximately half way between setting y1 and setting y2. The reader unit is then positioned such that the angle of incidence between the reader unit and the object plane is at setting y3. For example, a sixth image 730 shown in FIG. 7B illustrates that when the angle of incidence is set at the setting y3, the areas of brightness 710 are not imaged and the TOAD lighting arrays are aligned for the y-direction.

In one embodiment, the measurements made in the y-direction are made while the angle of incidence in the x-direction is set at the setting x3. Then, once the angle of incidence in the y-direction is set at the setting y3, the measurements made in the x-direction are re-measured and a new value for the setting x3 is determined.

In one embodiment, the mirror used to align the TOAD lighting arrays is spun during an imaging process to evaluate the cosmetic quality of the reader unit. Dirt, dust, coating defects, and other imperfections on the reader unit's lenses and internal mirrors are difficult to distinguish from dirt, dust and other imperfections in the external mirror used to align the TOAD lighting arrays. Spinning the external mirror identifies defects that are attributable to the reader unit. For example, when the external mirror is spun, the areas of brightness 710 shown in FIGS. 7A and 7B become low intensity streaks. However, any bright spots due to internal dirt, dust, coating defects, and other imperfections do not become streaks when the external mirror is spun. Thus, the internal imperfections of the reader system can be distinguished from the external imperfections of the spinning mirror.

D. Separating Front and Rear Lens Groups

A wafer ID system generally comprises basic blocks including, for example, a video camera, a lens, and a light source. Such wafer ID systems may provide some combination of brightfield illumination, darkfield illumination, and narrow-angle darkfield illumination by placing the light source slightly off-axis from the lens and camera (e.g., typically between approximately 5 degrees and approximately 7 degrees) and providing an associated baffle or baffles to prevent a direct view of the light source in reflection by the mirror-like surface of the subject wafer.

It is common in these types of systems to provide a selection of conventional, often "off-the-shelf," video lenses to provide the system with a variety of fields of view. For example, a field of view of about 30 mm for reading alphanumeric serial numbers such as those described within the SEMI M13 specification, and a field of view of about one-half that for reading 2DID serial numbers, which are generally much smaller and benefit from the increased magnification that corresponds to a smaller field of view.

As discussed above, the '949 patent teaches the incorporation of the narrow-angle darkfield light source within the telecentric optical imaging system 100 shown in FIG. 1A. Thus, the same optical system that is used to form an image of the serial number to be read is also used to closely control the geometry of the light. By disposing the light source 118 about the telecentric stop 116, the properties of the lenses 108, 110 can be used to bring the darkfield illumination to within a range between approximately 1 degree and approximately 2 degrees of the optical axis 111 while remaining blind to a direct reflection of the lighting elements. Further, the properties of the lenses 108, 110 are used to maintain the uniformity of this relationship across the entire field of view.

A problem posed with the system disclosed in the '949 patent is that the lenses 108, 110 are much more sophisticated than those used in conventional imaging systems. At least one optical element of the system is made specifically for a particular system and is not available "off the shelf" because of the unique requirements of the lenses 108, 110. For example, one unique requirement is that the telecentric field lens 110 be a meniscus lens having radii of curvature of both external surfaces less than or equal to the distance between the telecentric aperture and the nearest surface of the telecentric field lens 110.

In one embodiment disclosed herein, a specific design method provides the ability to change the magnification of the optical imaging system 100 by changing a relatively small optical subsystem, not the entire optical system. According to one embodiment, the magnification of the system can be varied by exchanging the rear lens group 108 with little or no impact on the entire system other than the desired change in system magnification.

By way of comparison with the embodiments disclosed herein, if a conventional design approach is used to design the optical imaging system 100, a skilled person would make design choices of various radii of curvature for each lens element, various glass types for each lens element, and various thicknesses and spacings for each lens element. However, the family of solutions for such a conventional design approach is inseparable. That is, the rear lens group 108 and the front telecentric field lens 110 must be treated as a single unit if an acceptable limit of optical performance is to be achieved. Following this design approach, if one is to offer a similar system with a different magnification, then the rear lens group 108 of the second system would be designed to complement the telecentric field lens 110 of the first system at the very least. Alternatively, one could redesign the entire system to achieve the new field of view. This alternative approach might be necessary if the second field of view is greater than that of the first field of view.

In one embodiment, a method to minimize cost, parts count, and development time includes designing the optical imaging system 100 for a larger field of view (e.g., lower magnification) first. This ensures that the telecentric field lens 110 is sufficiently large for any subsequent systems. Then, the design is made separable by deviating from conventional design and production methods that use generally spherical curves and conic sections to one that uses an aspheric curve of the form:

$$Z = \frac{CY^2}{1 + \sqrt{1 - (1+K)C^2Y^2}} + A_1Y^2 + A_3Y^3 + A_4Y^4 + A_5Y^5 + A_6Y^6 + \ldots + A_nY_n.$$

The first part of the above equation is a standard description of a spherical or conic section lens surface. Z is the displacement along the optical axis of a particular curve, known in the art as "sag." Y is a radial distance from the optical axis. C is the curvature (reciprocal of the radius of curvature) and K is the conic constant. $K<-1$ for hyperbolas, $K=-1$ for parabolas, $-1>K<0$ for ellipsoids, $K=0$ for spherical surfaces, and $K>0$ for oblate ellipsoides. The series $A_n$ are the aspheric coefficients and modify the sag Z as a function of the radial distance to the axis to the power n denoted here as $Y^n$. If only even n are used in the coefficients $A_nY^n$, as is used in one embodiment, then the resultant curvature and lens using that curve is called an even asphere. If both the odd and even n are used, then the curve and the lens using that curve is called an odd asphere. A more general case of the odd asphere is presented here.

Skilled persons generally avoid such complex curves because they are generally expensive to commercially produce. However, it was determined that the optical character of a molded polymer lens would be adequate for a separable design. A molded polymer lens according to one embodiment provides a low-cost lens with a complex curvature that allows it to be separated in design from other lenses in the system. With a separable design implemented using an aspheric curve on the front telecentric field lens 110, the telecentric field lens 110 can be sufficiently well corrected and considered in isolation from the rest of the system.

Independently correcting the telecentric field lens 110 permits the selection of the rear lens group 108 such that it is independently well corrected. In one embodiment the rear lens group 108 includes commercial objective lenses that meet the requirements of having the appropriate focal length to achieve the desired system magnification, an image circle of adequate size to cover the selected camera sensor, and being of a design compatible with having the system stop 105 defined between the rear group and the front lens An example of such a lens for the rear lens group 108 is one that is telecentric in the rear and has its system stop 105 at the front of the lens. Such lenses are sometimes called pinhole lenses because the front aperture can be aligned with a pinhole for covert surveillance. By designing the telecentric field lens 110 to be individually well corrected using an aspheric first surface and by careful selection of pinhole rear lenses for the rear lens group 108, a system with multiple magnifications can be offered whereby the optics comprise a single low cost plastic element with the aspheric surface for the telecentric field lens 110 and a variety of commercial pinhole lenses for the rear lens group 108.

It will be obvious to those having skill in the art that many changes may be made to the details of the above-described embodiments without departing from the underlying principles of the invention. The scope of the present invention should, therefore, be determined only by the following claims.

The invention claimed is:

1. An imaging system for imaging a defect on a planar specular object, the imaging system comprising:
    a telecentric lens having a sufficiently aspherical surface such that the telecentric lens is substantially corrected for an optical aberration;
    a telecentric stop including an aperture therein to block light reflected from the planar specular object while allowing light reflected from the defect to pass through the aperture; and
    a lens group having a system stop positioned between the telecentric stop and the lens group, the lens group being substantially corrected for the optical aberration independent of the telecentric lens.

2. The imaging system of claim 1, further comprising a camera for imaging the planar specular object through the telecentric lens, the telecentric stop, and the lens group.

3. The imaging system of claim 2 wherein the camera comprises a complementary metal-oxide semiconductor (CMOS) sensor.

4. The imaging system of claim 3 wherein the imaging system has a depth of focus of approximately ±10 mm.

5. The imaging system of claim 1, wherein the telecentric lens comprises a molded polymer.

6. The imaging system of claim 1, wherein the optical aberration comprises spherical aberration.

7. The imaging system of claim 1, wherein the lens group comprises a pinhole lens.

8. The imaging system of claim 1, further comprising a source of illumination positioned to illuminate the planar specular object along an axis of the telecentric lens.

9. The imaging system of claim 1, wherein the source of illumination comprises two or more concentric arrays of light emitting diodes (LEDs).

10. The imaging system of claim 9, wherein successive concentric arrays in the two or more concentric arrays of LEDs alternate between being tangentially arranged and radially arranged with respect to a common center point.

* * * * *